(12) United States Patent
Ward et al.

(10) Patent No.: US 6,875,386 B1
(45) Date of Patent: Apr. 5, 2005

(54) NEOVASCULARIZATION PROMOTING MEMBRANE FOR BIOIMPLANTS

(75) Inventors: Kenneth Ward, Portland, OR (US); Jerome J. Boogaard, Forest Grove, OR (US)

(73) Assignee: iSense Corp., Portland, OR (US)

( * ) Notice: Subject to any disclaimer, the term of this patent is extended or adjusted under 35 U.S.C. 154(b) by 0 days.

(21) Appl. No.: 10/364,691

(22) Filed: Feb. 11, 2003

Related U.S. Application Data

(62) Division of application No. 09/441,642, filed on Nov. 17, 1999, now abandoned.

(51) Int. Cl.[7] .............................. B29D 19/09; A61E 2/02
(52) U.S. Cl. ................... 264/154; 623/23.3; 623/23.76; 604/19; 604/175; 606/76
(58) Field of Search ..................... 210/500.27, 500.36, 210/500.4; 264/154, 152, 153, 155; 604/175, 19, 31; 606/76; 623/11.1, 23.3, 59, 23.76; 156/510; 424/472, 424

(56) References Cited

U.S. PATENT DOCUMENTS

| | | | |
|---|---|---|---|
| 4,392,848 A | * | 7/1983 | Lucas et al. ................ 604/500 |
| 4,832,997 A | * | 5/1989 | Balanzat et al. ............. 428/131 |
| 4,923,608 A | * | 5/1990 | Flottmann et al. ...... 210/500.25 |
| 5,362,525 A | * | 11/1994 | Nishii et al. ................ 427/554 |
| 5,753,014 A | * | 5/1998 | Van Rijn ........................ 96/12 |
| 6,427,419 B2 | * | 8/2002 | Owensby ...................... 53/396 |
| 6,716,444 B1 | * | 4/2004 | Castro et al. ................ 424/422 |
| 6,726,727 B2 | * | 4/2004 | Scott et al. .................. 522/161 |

* cited by examiner

*Primary Examiner*—Ana Fortuna
(74) *Attorney, Agent, or Firm*—Law Office of Timothy E. Siegel; Timothy E. Siegel

(57) ABSTRACT

A method of producing a biocompatible microporous membrane comprising the steps of providing a biocompatible membrane and using an energy beam to form a set of pores having a minor axis of less than 15 μm through the biocompatible membrane. One embodiment includes the steps of producing a first layer of material, defining a first set of pores; producing a second layer of material, defining a second set of pores and wherein the second set of pores is defined so as to cooperatively engage the first set of pores; and aligning and joining the first layer of material to the second layer of material to form a laminated membrane, having through-passageways formed by the first set of pores at least partially aligned with the second set of pores.

10 Claims, 7 Drawing Sheets

NEOVASCULARIZATION PROMOTING MEMBRANE FOR BIOIMPLANTS

RELATED APPLICATIONS

This application is a divisional of Ser. No. 09/441,642 filed Nov. 17, 1999 now ABN.

FIELD OF THE INVENTION

The present invention pertains to the field of bioimplants, particularly to the field of preventing foreign body reactions, especially fibrosis, around bioimplants. In a particular embodiment, the invention pertains to the field of prolonging the useful life of an implanted biosensor by reducing or eliminating the fibrous capsule that results from the body's response to the presence of the implant.

BACKGROUND OF THE INVENTION

Materials are implanted into a human or animal body for a variety of purposes. Such implants include prosthetic devices, electrical leads, vascular grafts, and biosensors. Generally, most implants provoke a classic foreign body reaction. This reaction includes an acute inflammatory response of inflammatory cells and fibroblasts followed by a decrease in the acute inflammatory reaction and the production of a collagen. Eventually, the fibroblasts mature into fibrocytes, an avascular fibrous capsule is formed which walls off the implant, and the foreign body reaction becomes quiescent.

With certain types of implants, notably electrical leads and biosensors, the foreign body reaction with its resultant isolation of the implant from bodily tissues and fluids, is detrimental.

In the case of an electrical lead for stimulating tissue, the presence of a fibrotic capsule surrounding the lead dampens and decreases the output of the lead. This often can be overcome by increasing voltage. With biosensors, however, the situation differs. A biosensor may measure the presence of analytes in tissue fluid adjacent to the sensor. If an avascular fibrous capsule prevents the analyte from reaching the sensor, the sensor can no longer measure the level of the analyte even though the sensor itself is functioning properly. Increasing the sensitivity of the sensor, although somewhat analogous to increasing the voltage of an implanted electrical lead, does not correct the problem if the sensor is sealed off from tissue fluid containing the analyte.

Researchers have investigated various ways to try to reduce or eliminate the foreign body reaction around an implant and its resultant fibrous capsule and to increase neovascularization around the implant.

Beisang et al., *Aesthetic Plastic Surgery*, 16:83–90 (1992), reported that rough textured surfaces allow a mechanical bond and enhanced tissue adhesion at the host/implant interface which minimizes the thickness of a fibrous capsule. Den Braber et al, *Biomaterials*, 17:2037–2044 (1996), invest gated various characteristics of microgrooved surfaces, including groove width, groove depth, and ridge width, to determine the morphology of fibroblasts on implants having varying grooved textures. They reported that on surfaces having a ridge width of 4.0 micrometers or less, fibroblasts were highly oriented, whereas with a ridge width of greater than 4.0 micrometers, the fibroblasts are arranged in a random cellular orientation. They further found that groove depth and groove width did not affect cellular orientation.

Brauker et al., *J. Biomedical Materials Res.*, 29:1517–1524 (1995), investigated over 150 commercial membranes and concluded that the surface chemistry of an implanted membrane is not responsible for the degree of neovascularization around the implant. They concluded that membrane geometry, particularly the size of pores on a membrane, correlates with the degree of neovascularization adjacent to the membrane. They reported that implanted membranes having pores of 0.02 to 1 micrometer were bordered by a classical foreign body response without close vascular structures. In contrast, implanted membranes with pores of 3 or 5 micrometers, large enough to permit passage of host inflammatory cells, were bordered by a close association of vasculature. Brauker further disclosed that neither the structure of the pores nor the means of producing the pores is critical in the promotion of neovasculature. Both cellulosic and acrylic copolymer membranes, in which the pores are produced by solvent evaporation, and expanded polytetrafluoroethylene (ePTFE) membranes, in which the pores are produced by stretching, were effective in promoting neovascularization as long as the pores were of a sufficient size.

Sharkawy et. al., *J. Biomedical Materials Res.*, 40(4):586–597 (1998) reported that PTFE implants having mean pore sizes of 5.0 and of 0.5 micrometers produced similar fibrotic capsules with little vascularity. They found that implanted polyvinyl alcohol (PVA) membranes having pore sizes of 5.0 and 60 micrometers were surrounded by sparse, randomly oriented tissue that resembled normal subcutaneous tissue and contained evidence of a granulomatous response. They further reported that implanted PVA membranes having a mean pore size of 700 micrometers were perceived by the body as being multiple implants as separate fibrous capsules surrounded each nodule of solid PVA between pores. From this data, Sharkawy concluded that mean pore size of 60 micrometers is optimal for inducing vascularity resembling granulation tissue. This objective might be achieved by providing adjacent to the sensor a scaffold of an open porous network with an average pore size in the range of cellular dimensions to incite fibrovascular ingrowth and sustained vasculature months after implantation.

Salzmann et al., *J. Biomedical Materials Research*, 34:463–476 (1997), reported that implanted expanded PTFE (ePTFE) membranes having an average internodal distance (pore size) of 60 micrometers produced more rapid endothelialization than did ePTFE membranes having an average pore size of 30 or of 100 micrometers. Further, the fibrous capsule surrounding the 60 micrometer pore size ePTFE was thinner than for the smaller and larger pore size ePTFE membranes.

Presently, microporous membranes are made by several methods, depending on the composition of the membrane. Porous PTFE membranes are made by expansion, that is by stretching, of the fabric of the membrane to form expanded PTFE ("ePTFE"). As shown in FIG. 1, ePTFE contains a tremendous variability of fibril 11 length, interfibrillar distance, size of islands or nodes 12, and internodal distance or pore size 13. FIG. 2 shows a porous polymer matrix in which the pores 15 are made by a gas foaming technique. The marked variability of the pore size and structure is evident in FIG. 2. Although with salt crystal poration and neutron bombardment the pore sizes are quite uniform, nonuniform pore spacing results in an unpredictable structure with an unpredictable tendency to promote neovascularization.

The variability of pore size and distribution in presently available membranes results in unpredictability of the foreign body reaction that is elicited by implantation of such membranes. Portions of such present-day membranes may or may not elicit the classical foreign body reaction with development of a fibrous capsule. Accordingly, an important need still exists for a membrane for a bioimplant that predictably encourages neovascularization and inhibits the formation of a fibrous capsule. This need is most strongly felt in regards to implanted analyte sensors, such as glucose sensors, that decline in accuracy within a brief span of days to weeks following implantation due to the development of a fibrous capsule around the implant that limits diffusion of the analyte to the sensor.

Additionally, although biological electricity sensors have been disclosed that included a microporous membrane covering the sensing surfaces, it appears that no similar analyte sensor has been taught. Analyte sensors are typically far more delicate than electricity sensors and so a much more complete level of neovascularization would be necessary to protect such a sensor.

BRIEF SUMMARY OF THE INVENTION

In a first separate aspect the present invention is a method of producing a biocompatible microporous membrane comprising the steps of providing a biocompatible membrane and using an energy beam to form a set of pores, having a mean area of less than 500 $\mu m^2$ through the biocompatible membrane.

In a second separate aspect the present invention is a biocompatible membrane portion defining a set of pores, each having an individual pore surface area and collectively having a total pore surface area and defining a set of islands each having an island surface area and further defining a membrane material surface area and fitting the following set of criteria:
 (a) at least 75% of said total pore surface area is in pores that each have a minor axis 1.5 $\mu m$ and 15 $\mu m$;
 (b) at least 75% of said membrane material surface area is in islands that each have a minor axis of between 2.5 $\mu m^2$ and 25 $\mu m$;
 (c) the pore surface area is between 1% and 60% of the membrane portion surface area.

In a third separate aspect the present invention is an analyte sensor having a sensing surface that is covered with a microporous neovascularization promoting membrane.

In a fourth separate aspect the present invention is a method of manufacturing an analyte sensor having sensing surfaces coated with a microporous, neovascularization promoting membrane, comprising the steps of coating the sensing surfaces with substantially nonporous membrane and perforating the substantially nonporous membrane as it resides over the sensing surface.

In a fifth separate aspect the present invention is a method of producing a laminated microporous membrane, comprising the steps of producing a first layer of material, defining a first set of pores; producing a second layer of material, defining a second set of pores and wherein the second set of pores is defined so as to cooperatively engage the first set of pores; and aligning and joining the first layer of material to the second layer of material to form a laminated membrane, having through-passageways formed by the first set of pores at least partially aligned with the second set of pores.

The foregoing and other objectives, features, and advantages of the invention will be more readily understood upon consideration of the following detailed description of the invention, taken in conjunction with the accompanying drawings.

DETAILED DESCRIPTION OF THE PREFERRED EMBODIMENTS

Figure 1:
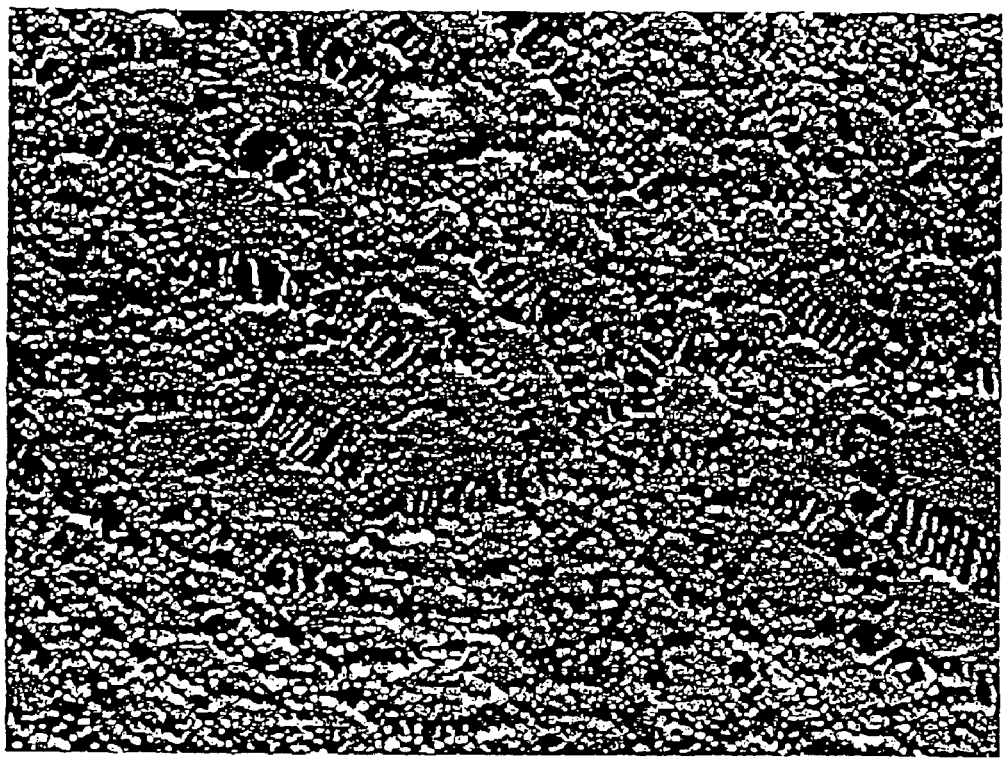
FIG. 1 shows a scanning electromicrograph of a prior art film of expanded PTFE.
Figure 2:
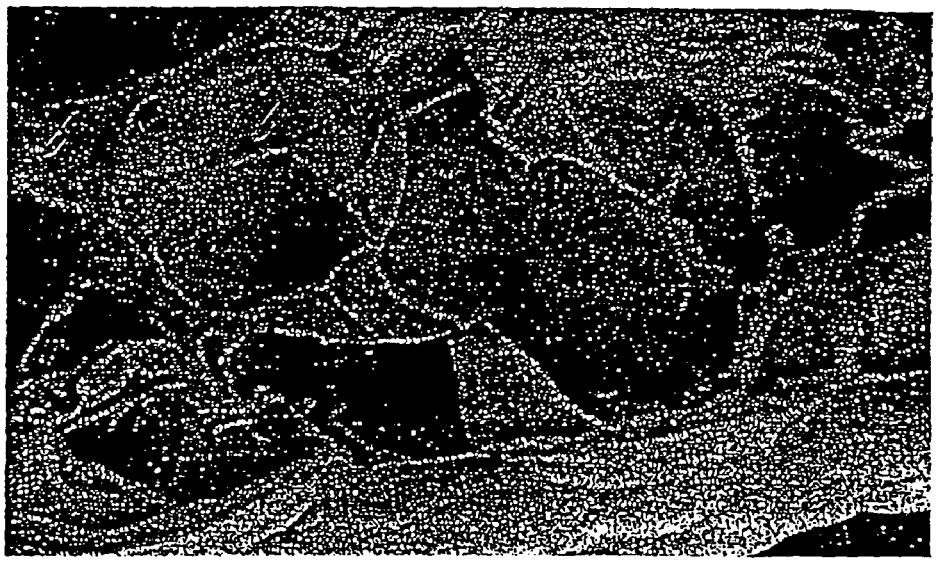
FIG. 2 shows a scanning electromicrograph of a prior art polymer matrix fabricated using the gas foaming method.
Figure 3:
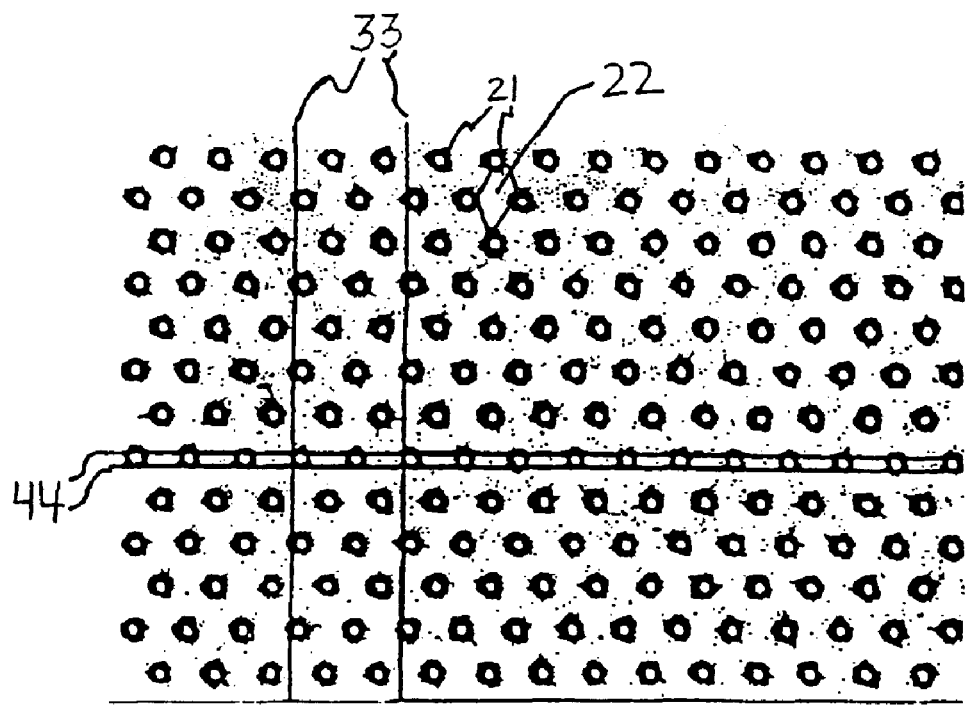
FIG. 3 shows a light micrograph of a microporous membrane according to the invention.

A first preferred embodiment, the invention is a microporous membrane in which the pores are substantially uniform in size and spacing. FIG. 3 shows a light micrograph of a preferred embodiment of the membrane of the invention in which the pores 21 are 5 micrometers in diameter and separated by interpore islands 22 that are 20 micrometers across. Vertical calibration cross-hairs 33 are separated by a distance of 50 micrometers and horizontal calibration cross-hairs 44 are separated by a distance of 5 micrometers.

The thickness of the membrane may vary depending on its intended use. Its thickness should be sufficient to permit the membrane to be worked with without tearing or folding. It should be thin enough so as not to interfere with the function of the underlying bioimplant, such as a sensor. Typically, the membrane is between about 10 to 200 micrometers thick. Preferably, the thickness of the membrane is between 15 and 100 micrometers. Most preferably, a single-layer microporous membrane of the invention has a thickness of between about 20 to 40 micrometers and a three-layer laminated microporous membrane of the invention has a total thickness of about 75 to 90 micrometers.

The photomicrograph of FIG. 3 is of a hydrophilic cellulose membrane. The chemical composition of the membrane is immaterial however, so long as it is substantially chemically inert to chemicals found within bodily tissues. Examples of suitable biocompatible materials for the microporous membrane of the invention include tetrafluoroethylene/hexafluoropropylene copolymer (FEP), polytetrafluoroethylene (PTFE), polycarbonate urethane with or without polysiloxane modification of end groups, polyvinyl alcohol, cellulose acetate, polyvinyl difluoride, polysulfone, polyester, polypropylene, cellulose nitrate, polycarbonate, nylon, polyethylene, and acrylic copolymers. It is conceived that the microporous membrane of the invention may be constructed of materials other than plastic polymers, such as glass.

Figure 7:
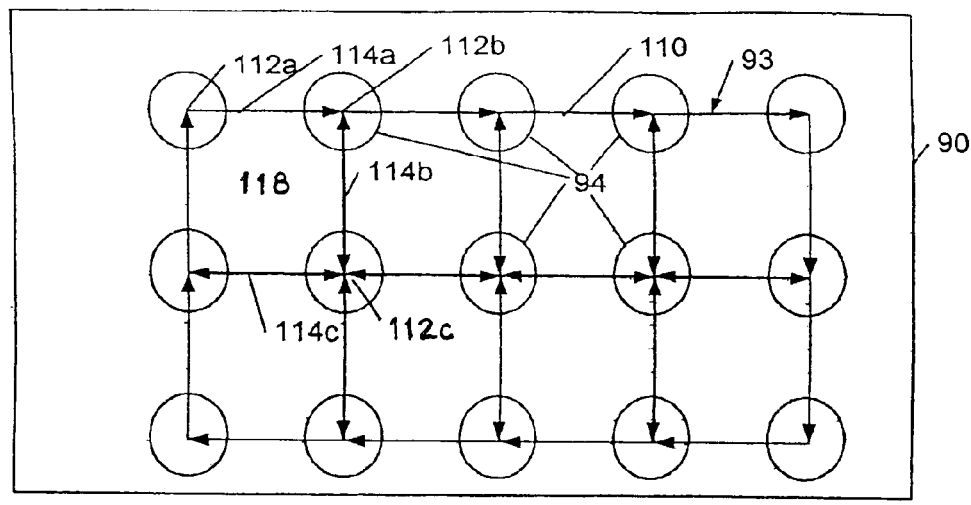
FIG. 7 shows a top view of a membrane defining a periodically situated set of pores presented to help define various terms.
Figure 8:
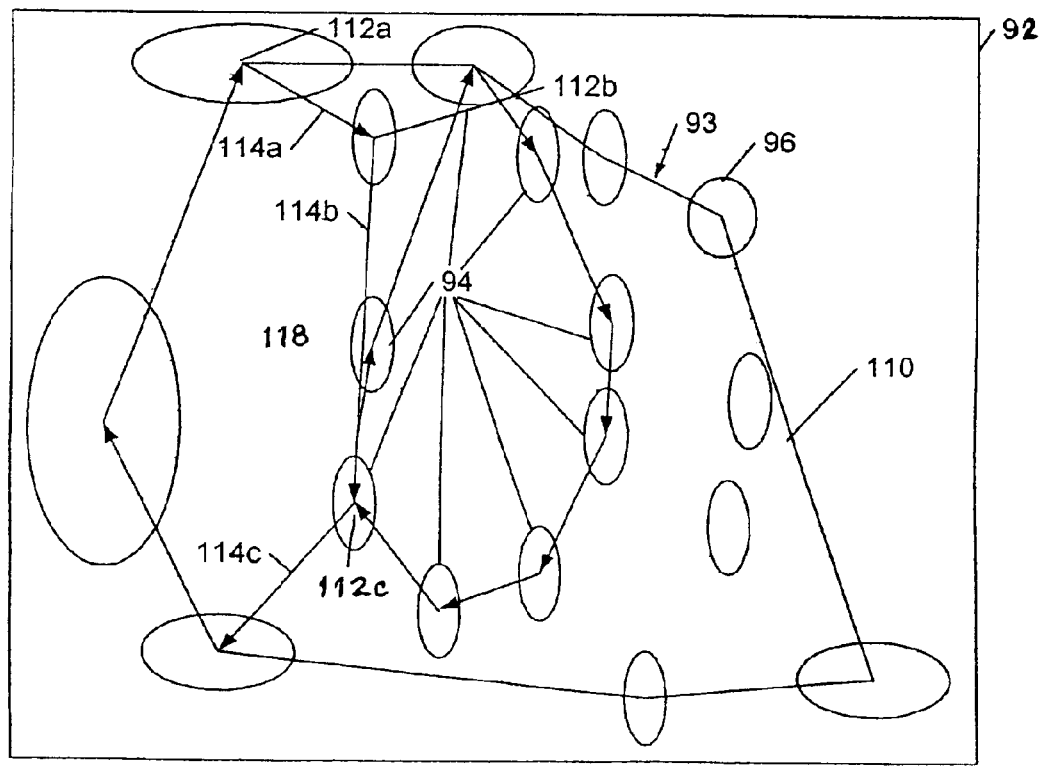
FIG. 8 shows a top view of a membrane defining a scattered set of pores, presented to help define various terms.

In order to define the sort of membrane that is most useful in the formation of neovascularized tissue, it is first necessary to define a few terms. FIGS. 7 and 8 both show a top view of a membrane 90 and 92, respectively, (within membranes 90 and 92 like elements are assigned identical reference numbers and are discussed together) having a neovascularization promoting portion 93 that defines a set of pores 94. The pore periphery 110, which defines the active membrane area 93, is a boundary line drawn from pore center 112 to pore center 112 drawn so that no pore center lies outside of the periphery 110. Membrane material may be divided by starting at a random pore center 112a (typically on the pore periphery) and drawing a vector 114a to the nearest neighbor pore 112b. Next, another vector 114b is drawn, this time from the nearest neighbor pore 112b to its nearest neighbor 112c that can be found by turning to the right, relative to the previously defined vector 114a. This process of drawing vectors 114 is continued until the original pore center 112a is reached. The area surrounded by the vectors is defined as an island 118. The process is continued until all the area within the periphery has been divided into islands 118. No two islands 118 may overlap. The membrane material surface area is the surface area within the periphery that is left after subtracting out the pores. The pore surface area is the surface area of all the pores added together. The individual pore surface area is the surface area of a particular individual pore. The island surface area is the surface area of a particular single island, it does not include any of the pore surface area that falls within the shape created by drawing vectors from pore center to pore center.

In one preferred embodiment a membrane fits the following set of criteria:

1. at least 75% of said total pore surface area is in pores that each have a minor axis 1.5 $\mu$m and 15 $\mu$m;
2. at least 75% of said membrane material surface area is in islands that each have a minor axis of between 2.5 $\mu$m$^2$ and 25 $\mu$m; and
3. The pore surface area is between 1% and 60% of the surface area within the periphery.

This design appears to be well suited for stimulating the growth of neovascularized tissue because both the island size and the pore size are small enough so that immune system cells do not recognize the presence of a foreign body. Moreover, the pores are small enough, as measured by their minor axes, to prevent macrophage cells from slipping through the membrane. The minor axis length appears to be the most crucial size dimension for stopping the passage of macrophage cells. It also appears that a membrane fitting these criteria could not be produced by prior art techniques.

In a preferred embodiment, the pores 94 are formed by ablation of the membrane 90 using an energy beam such as a laser or an electron beam. In one preferred embodiment a frequency quadrupled nd:YAG laser (ESI model 4420 Micromachining System, Electro Scientific Industries, Beaverton, Oreg.) having a wavelength of 266 nm is used for the laser ablating. For pores larger than 15 $\mu$m in diameter ablation is performed repeatedly for each individual pore (this process is known as "trepanation,") to cut out the outline of the pore. For pores smaller than about 15 $\mu$m is diameter, a frequency quadrupled nd:YAG laser can be used to directly ablate the pore rather than ablating the outline. In another preferred embodiment a mask is used in conjunction with a $CO_2$ laser to form the pores. With this technique a plurality of pores can be formed simultaneously. An excimer laser could also be used with this application. In an additional masking technique a mask could be used to prevent the ablation of non-pore designated areas during a plasma etch of a base membrane. For the purposes of this application the process of plasma projecting through a mask pore is considered to be a type of energy beam.

The microporous membrane may be composed of a single layer or may be of multiple layers, such as 2 to 4 laminated layers or more. If composed of multiple layers, the total thickness of the membrane should be as stated above. The thickness of each of the individual layers is immaterial, although extremely thin membrane layers may be more difficult to work with due to the tendency to tear or to fold.

Figure 4:
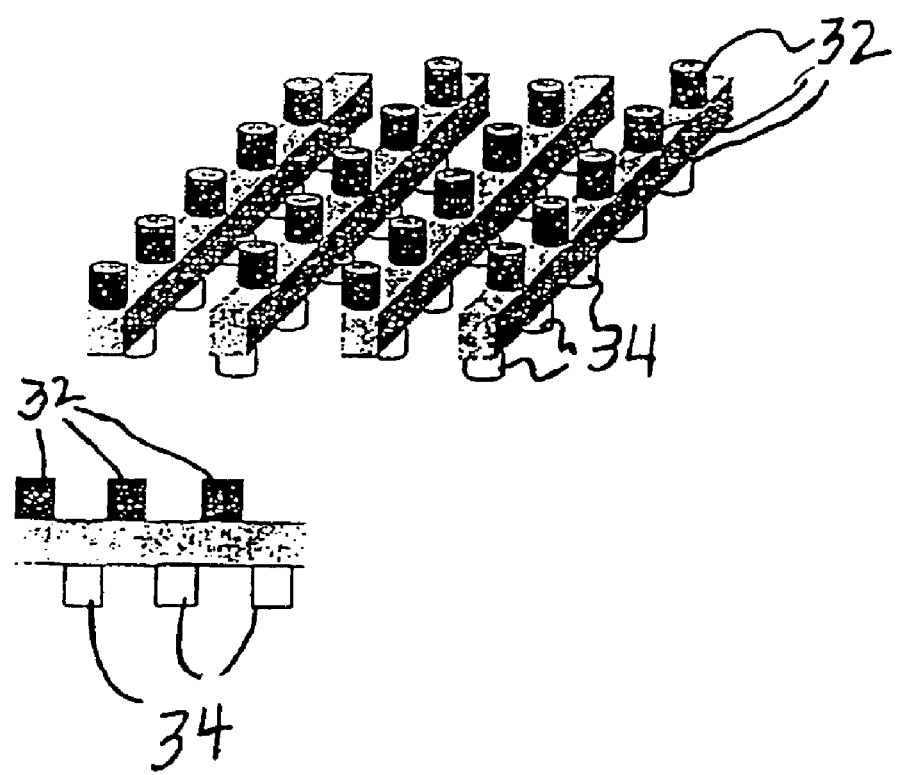
FIG. 4 shows a preferred embodiment of the arrangement of pores in a triple laminated microporous membrane according to the invention.

Multiple layers may contain linearly oriented pores so that the pores of the several layers form a straight column. Preferably, the pores throughout the multilayered membrane are in a serpentine or sponge-like three dimensional interconnected channel structure. FIG. 4 shows a diagrammatic representation of one embodiment of the multilayered microporous membrane of the invention in which the membrane contains three layers with interconnected serpentine channels. In this representation, the void spaces are shown as positive structures and the actual material of the membrane is not shown at all to emphasize the arrangement of the void spaces.

As shown in FIG. 4, a top lamina contains vertical holes 32 that extend from the outer to the inner surfaces of this lamina. A bottom lamina likewise contains vertical holes 34 that extend from the outer to the inner surfaces of this lamina. Preferably, as shown, the vertical holes 32 of the top lamina are offset from the vertical holes 34 of the bottom lamina. These two lamina are separated by a middle lamina that contains horizontally oriented channels that connect the holes 32 and 34 of the other lamina. In this way, the pores of the multilayered membrane have a serpentine, interconnected configuration.

The microporous membrane of the invention having one or more layers may be produced and may be adhered to a bioimplant, such as a biosensor, in various ways. Polymer sheets, such as PTFE or cellulose, are available for purchase or may be created, such as by crosslinking a polymer such as PVA onto a flat surface followed by thermal cure. Other polymers, such as polycarbonate urethane do not require crosslinking. In order to maintain the sheets perfectly flat during poration, it is preferred to adhere the sheets to a solid substrate during this process.

Because the porous membranes are fragile, especially those of high pore density such as where the pore size is as large as the interpore distance, it may be desirable to place a polymer backing net on the substrate sheet during the laser poration process. A netting, such as polyethylene mesh, may be bonded to the membrane with a silicone adhesive. Because the backing is widely porous, it does not retard analyte influx.

Alternatively, pores may be produced by sleeve poration. In this method, pores are created on a cylindrical substrate. A chemical releasing agent is coated over a mandrel wire, such as a 250 micrometer wire, a bioprotective polymer is dip-coated over the wire, then pores are laser-machined in the polymer sleeve. The releasing agent is then dissolved to permit the sleeve to be removed from the wire. With certain polymers, such as the fluorocarbon polymer FEP, sleeves may be created by direct extrusion. In this way, hollow FEP tubes may be formed, such as about 250 micrometers inside diameter and a wall thickness of about 25 to 35 micrometers. The formed sleeves, following dissolving of the releasing agent, are placed over a needle sensor of suitable diameter.

Alternatively, pores may be created in a membrane that has been already directly coated upon a sensor, such as a glucose sensor. This method obviates the need to add and remove a releasing agent, to remove the sleeve from a mandrel wire, and to place it over the sensor after poration. If this approach is used, care must be taken to precisely regulate the depth of pores created by a laser to assure that the pores adequately penetrate the membrane while preventing the laser beam from boring into and potentially destroying the underlying structure of the sensor.

An nd:YAG laser lends itself to this type of machining. Light reflected from the object being machined may be used to control the laser, to avoid cutting into interior layers. In addition, dummy lasers could be added to prevent cutting too deep.

The following non-limiting examples are illustrative of the invention.

EXAMPLE 1

Uncoated (Prior Art) Bioimplants

Figure 5:
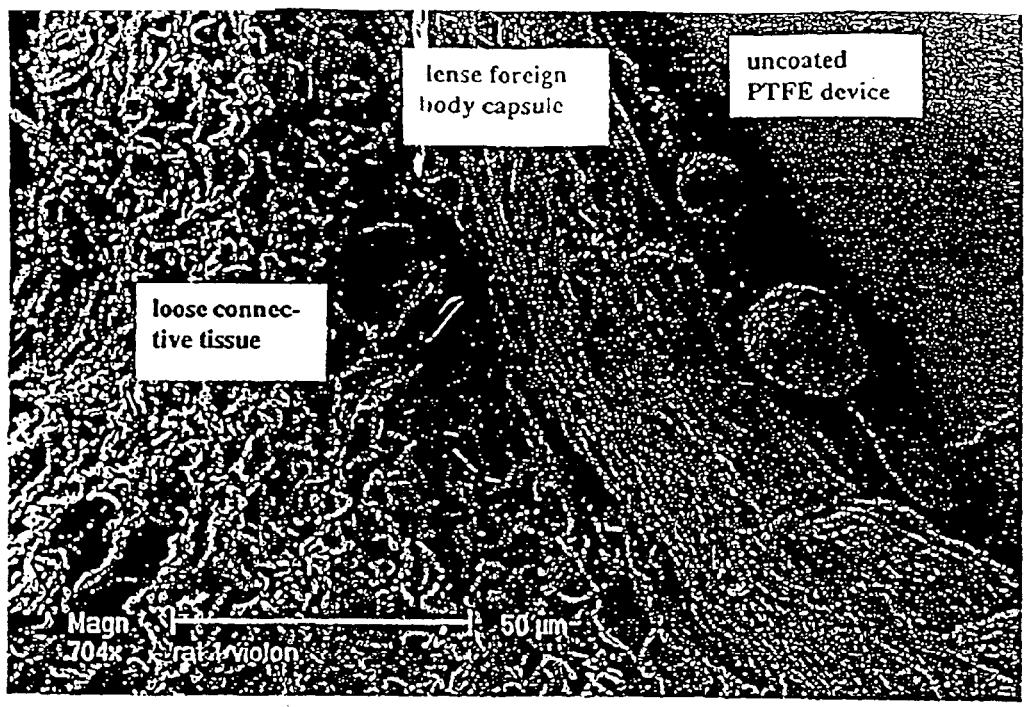
FIG. 5 shows a scanning electromicrograph of a prior art uncoated bioimplant with a dense fibrous foreign body capsule adjacent to the implant.

One-centimeter segments of a 20 gauge PTFE catheter were implanted in the subcutaneous tissues of a rat. After five weeks, the catheters and surrounding tissues were removed and examined microscopically, as shown in FIG. 5. The photomicrograph of FIG. 5 shows a well-defined dense collagen capsule 41 about 35 micrometers in thickness and having substantially parallel oriented fibers between the PTFE device 42 and the surrounding loose connective tissue 43. Two cells 44 are visible at the junction of the catheter and the fibrous capsule.

EXAMPLE 2

Bioimplants Coated in Accordance with the Invention

Figure 6:
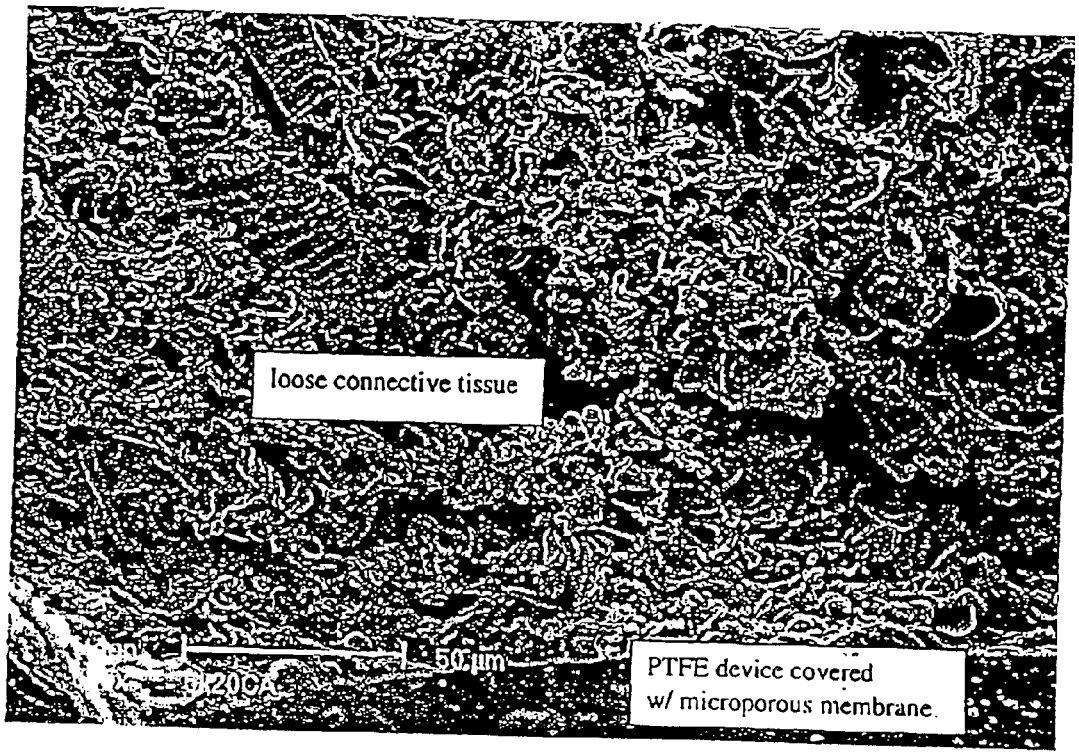
FIG. 6 shows a scanning electromicrograph of a bioimplant coated in accordance with the microporous membrane of the invention with loose connective tissue adjacent to the implant.

One centimeter segments of PTFE catheters as in Example 1 were wrapped with a porous cellulose acetate membrane in which substantially uniform 5 micrometer pores having a substantially uniform interpore distance of 20 micrometers were laser-machined. After 5 weeks, the catheter and surrounding tissues were removed from the rat and examined microscopically, as shown in FIG. 6. The photomicrograph of FIG. 6 shows loose connective tissue 51 extending to the border of the PTFE catheter 52. A fibrous foreign body capsule was not detected, indicating that the microporous membrane surrounding the implant prevented, or at least greatly reduced, the formation of a foreign body capsule around the implant.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of addressing a condition of a living body comprising the steps of:

(a) providing a work piece biocompatible membrane;

(b) using an energy beam to form a set of pores, having a mean area of less than 500 $\mu m^2$ through said biocompatible membrane, thereby producing a microporous membrane adapted to facilitate tissue in growth; and (c) providing an article that is adapted to be implanted in a living body;

(d) at least partially wrapping said article in said microporous membrane;

(e) implanting said at least partially wrapped article into said living body, thereby addressing said condition.

2. The method of claim 1 wherein said energy beam is a light beam.

3. The method of claim 2 wherein said light beam is a laser beam.

4. The method of claim 3 wherein said laser beam is formed in part by a mask placed over said biocompatible membrane.

5. The method of claim 3 wherein said laser beam is produced by a nd:YAG laser.

6. The method of claim 1 wherein said energy beam is formed by a plasma protruding through a pore defined on a mask placed over said biocompatible membrane.

7. The method of claim 1 wherein said living body implant is a catheter.

8. The method of claim 1 wherein said work piece biocompatible membrane is porous.

9. The method of claim 1 wherein said work piece biocompatible membrane is not porous.

10. The method of claim 1 wherein said microporous membrane adapted to facilitate tissue in growth has been substantially optimally engineered to facilitate tissue in growth.

* * * * *